United States Patent [19]
Fall et al.

[11] Patent Number: 5,578,278
[45] Date of Patent: Nov. 26, 1996

[54] TUBULAR REACTOR SYSTEM FOR DIRECT FLUORINATION

[75] Inventors: David J. Fall, Hudson, Wis.; Miguel A. Guerra, Woodbury, Minn.

[73] Assignee: Minnesota Mining and Manufacturing Company, St. Paul, Minn.

[21] Appl. No.: 455,096

[22] Filed: May 31, 1995

Related U.S. Application Data

[62] Division of Ser. No. 130,764, Oct. 4, 1993, Pat. No. 5,488,142.

[51] Int. Cl.$^6$ ........................................ B01J 10/00
[52] U.S. Cl. ................. 422/234; 560/227; 568/842; 570/134; 422/129
[58] Field of Search ...................... 422/129, 187, 422/234; 560/227; 568/842; 570/134

[56] References Cited

U.S. PATENT DOCUMENTS

| | | | |
|---|---|---|---|
| 4,113,772 | 9/1978 | Lagow et al. | 562/583 |
| 4,144,374 | 3/1979 | Lagow et al. | 428/334 |
| 4,226,796 | 10/1980 | Akred et al. | 558/41 |
| 4,261,916 | 4/1981 | Crosby | 558/33 |
| 4,328,369 | 5/1982 | Baldi et al. | 564/406 |
| 4,523,039 | 6/1985 | Lagow et al. | 568/615 |
| 4,675,452 | 6/1987 | Lagow et al. | 568/601 |
| 4,686,024 | 8/1987 | Scherer, Jr. et al. | 204/157.95 |
| 4,755,567 | 7/1988 | Bierschenk et al. | 525/409 |
| 4,859,747 | 8/1989 | Bierschenk et al. | 525/409 |
| 4,943,595 | 7/1990 | Scherer, Jr. et al. | 514/722 |
| 5,053,142 | 10/1991 | Sorensen et al. | 210/742 |
| 5,093,432 | 3/1992 | Bierschenk et al. | 525/331.6 |
| 5,116,582 | 5/1992 | Cooper et al. | 422/186.3 |
| 5,120,459 | 6/1992 | Kolota et al. | 252/54 |
| 5,177,275 | 1/1993 | Baucom et al. | 570/175 |
| 5,183,649 | 2/1993 | Holmes et al. | 423/300 |
| 5,482,682 | 1/1996 | Tarancon | 422/188 |

FOREIGN PATENT DOCUMENTS

| | | |
|---|---|---|
| WO90/03409 | 4/1990 | WIPO. |
| WO90/06296 | 6/1990 | WIPO. |

OTHER PUBLICATIONS

Kramers, H. and Westerterp, K. R., *Elements of Chemical Reactor Design and Operation,* Academic Press, Inc. 1963, pp. 55–56 (1963).

Levenspiel, O., *Chemical Reaction Engineering,* John Wiley & Sons, pp. XI–XV, 99–116 (1967).

*Encyclopedia of Chemical Processing and Design,* p. 287 (1994).

Lagow, R. J., "Direct Fluorination: A New Approach to Fluorine Chemistry", *Progress in Inorganic Chemistry,* 26, pp. 161–210 (1979).

*Kirk–Othmer Encyclopedia of Chemical Technology,* 3d ed. vol. 10, pp. 636, 840–855, John Wiley & Sons (1980).

Hill, C. G., Jr. *An Introduction To Chemical Engineering Kinetics & Reactor Design,* John Wiley & Sons, pp. 245–274. 357 (1977).

*Primary Examiner*—Robert J. Warden
*Assistant Examiner*—E. Leigh Dawson
*Attorney, Agent, or Firm*—Douglas B. Little; Gary L. Griswold; Walter N. Kirn

[57] ABSTRACT

Direct fluorination of organics such as 1,8-dichlorooctane in tubular reactor. Inert liquid containing organic feed is circulated through tubular reactor with fluorine gas for a time and at a temperature sufficient to yield fluorinated organic. Preferably, liquid and gas phases are separated from reactor product stream containing inert liquid, fluorinated organic, and any unreacted organic is recycled to turbulent mixing zone upstream of reactor in which fresh organic feed is added; and fluorine is added to recycle stream at end of mixing zone. Flow in tubular reactor is turbulent. Rate of organic feed and fluorine addition to process are independent of each other. Among process advantages are: Freon solvents not required; good control of reaction exotherm; and HF scavengers not required. Process useful for partial or complete fluorination.

2 Claims, 1 Drawing Sheet

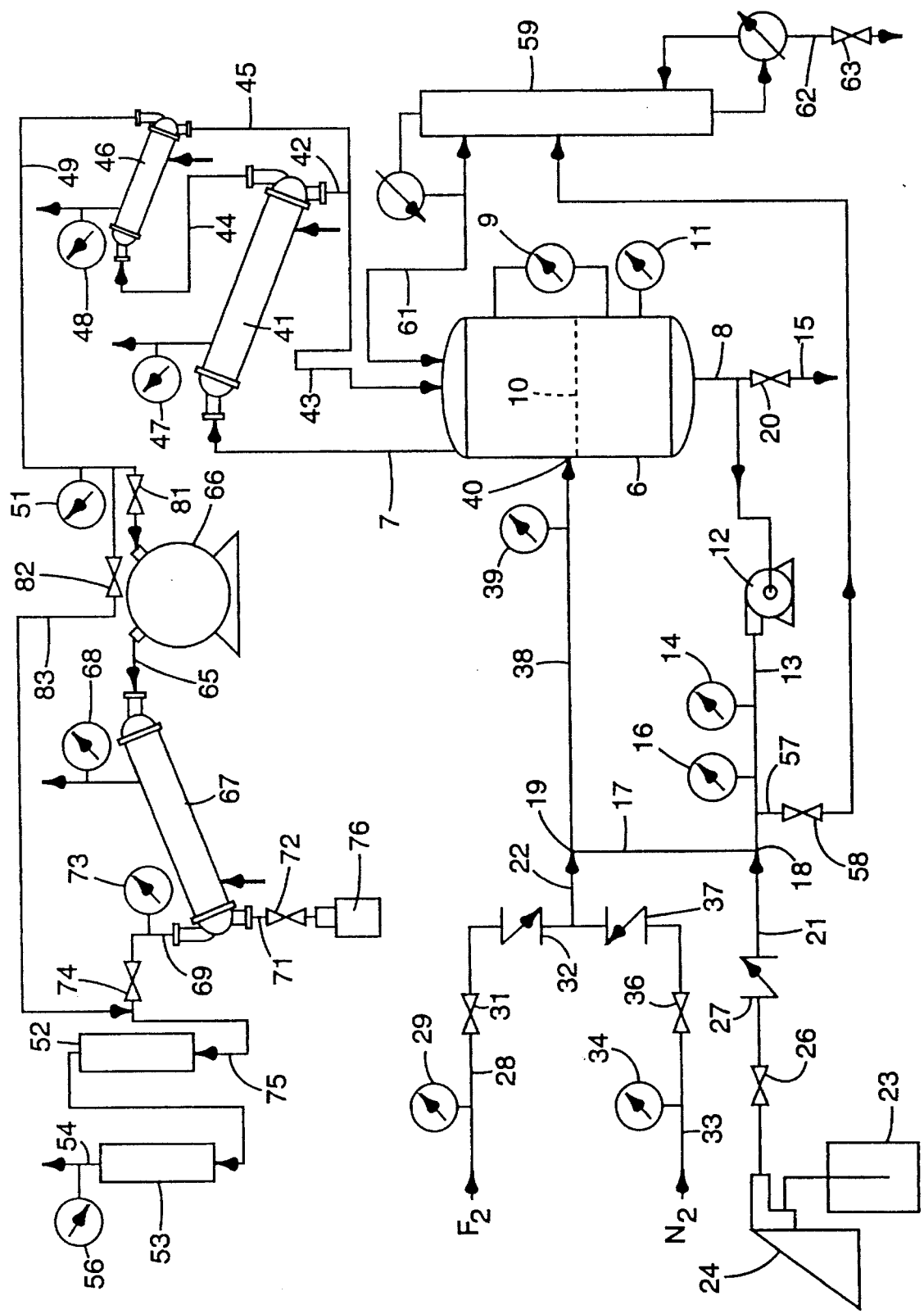

TUBULAR REACTOR SYSTEM FOR DIRECT FLUORINATION

This is a division of application Ser. No. 08/130,764 filed Oct. 4, 1993 now U.S. Pat. No. 5,488,142.

TECHNICAL FIELD

This invention relates to process and apparatus for fluorination of organic substances in inert liquid media. In another aspect, it relates to reactions carried out in a tubular reactor system containing a recycle loop.

BACKGROUND

Fluorochemical compounds (sometimes called organofluorine compounds or fluorochemicals) are a class of substances which contain portions that are fluoroaliphatic or fluorocarbon in nature, e.g., nonpolar, hydrophobic, oleophobic, and chemically inert, and which may contain other portions that are functional in nature, e.g., polar and chemically reactive. The class includes some commercial substances which are familiar to the general public, such as those which give oil and water repellency and stain and soil resistance to textiles. An industrial process for producing organofluorine compounds is the electrochemical fluorination process commercialized initially in the 1950s by Minnesota Mining and Manufacturing Company. This fluorination process, commonly referred to as the "Simons electrochemical fluorination process," is a highly energetic process which uses anhydrous hydrogen fluoride.

Another process for producing fluorochemical compounds is direct fluorination, but it is not significantly used today as an industrial process. In direct fluorination, the highly exothermic reaction of fluorine, $F_2$, with organic compounds is accompanied by quick evolution of heat and possibly by one or more of such phenomena as carbon—carbon scission or fragmentation, polymer formation, ignition, combustion, and violent explosion, the heat removal being the main problem in direct fluorination—see, for example, U.S. Pat. No. 4,523,039 (Lagow et al.) and Kirk-Othmer "Encyclopedia of Chemical Technology", 3rd Ed., Vol. 10, pages 636, 840–855, John Wiley & Sons, Inc., New York (1980). Various diverse fluorination methods or techniques which have been proposed to overcome problems in direct fluorination are dilution of the fluorine with an inert gas, use of low temperatures, use of inert solvents to dissipate heat, use of partially-fluorinated starting materials, dilution of the organic feed, use of hydrogen fluoride scavengers, and combinations of these techniques.

A review article on direct fluorination is that of Lagow et at. in *Progress in Inorganic Chemistry* 26, 161–210 (1979). Recent advances in direct fluorination are described, for example, in U.S. Pat. Nos. 4,859,747 (Bierschenk et at.), U.S. Pat. No. 4,973,716 (Calini et at.), U.S. Pat. No. 5,076,949 (Kalota et at.), U.S. Pat. No. 5,093,432 (Bierschenk et at.) and U.S. Pat. No. 5,177,275 (Baucom et al.) and the international application WO 90/06296 (Costello et al.), published Jun. 14, 1990 under the Patent Cooperation Treaty. The Bierschenk et al. patent and Costello et al. publication describe direct fluorination carried out in the liquid phase in stirred tank reactors using solutions or dispersions of various hydrogen-containing compounds or organic substances in inert liquid media, such as certain chlorofluorocarbons ("CCFCs"), e.g., Freon™ 113 1,1,2-trichlorotrifluoroethane (the use of which, while it readily dissolves a wide variety of organic substance, is being discontinued because of its atmospheric ozone depletion potential).

DISCLOSURE OF INVENTION

This invention provides a process and apparatus for the direct fluorination of a turbulent stream of organic substance in inert liquid medium, an embodiment of which uses a tubular reactor system that is illustrated schematically in the accompanying drawing.

The invention provides a process for producing fluorinated organic substances, for example, fluorinated octane or fluorinated poly(tetramethylene oxide) diacetate, said process comprising the steps of:

A. providing a reaction system comprising a tubular reactor and a means for conveying fluids through the reactor;

B. conveying through the tubular reactor a fluid stream comprising an organic feed which can be fluorinated (i.e., having hydrogen atoms bonded to carbon atoms which hydrogen atoms can be replaced by fluorine atoms) and an inert liquid medium;

C. introducing into the fluid stream of B. fluorine gas (which may be diluted with inert gas), the ratio of organic feed to fluorine being sufficient to obtain a chemical reaction between them; and D. fluorinating the organic feed in turbulent flow conditions and for a time sufficient to yield fluorinated product (i.e., organic feed in which some or all of the hydrogen atoms bonded to carbon atoms have been replaced by fluorine atoms).

The $F_2$ is introduced in step C. at sufficient pressure; into the reactor and at a flow rate independent of the flow rate of the liquid stream, thereby directly fluorinating the organic feed. The process preferably further comprises separating (preferably continuously) a gas phase comprising any unreacted fluorine, any inert gas, and byproduct hydrogen fluoride, and a liquid phase comprising the inert liquid medium, from the product stream (which can be a two phase stream) exiting the tubular reactor. Depending upon whether or not the fluorinated product from step D is gaseous or liquid under the conditions of the separation, it will go with the gas or liquid phase respectively.

Preferably, a recycle stream of the separated inert liquid medium is conveyed under turbulent flow conditions and mixed with additional organic feed. Preferably, the resulting mixed stream is reacted in the tubular reactor with fluorine gas. The process is continued to fluorinate the organic feed to the desired degree, that is, to ,obtain partially fluorinated or perfluorinated organic feed.

The direct fluorination process of this invention can be carried out in an economical manner by intermittently or continuously adding fresh organic feed to the continuously recycled or circulating stream of inert liquid medium, intermittently or continuously introducing the diluted fluorine to the tubular reactor, and intermittently or continuously recovering (e.g., by distillation) fluorinated product from a slip stream of the recycled stream of inert liquid medium containing the fluorinated product. The process can be practiced to produce a wide variety of fluorinated organic substances, normally liquid or gaseous, partially fluorinated or perfluorinated, functional or non-functional, low or high molecular weight. The fluorinated substances include a host of known fluorochemicals, such as fluorinated alkanes and ethers, having desirable properties such as heat stability, chemical inertness, and low surface energy. High yields of the liquid fluorinated products, and desired selectivity in the gaseous fluorinated products, are generally obtained by the process without requiring the use of very low reaction temperatures or partially-fluorinated starting materials and the process can be carded out in the absence of hydrogen fluoride scavengers, such as NaF and ultraviolet illumination (which is not required to initiate or sustain the fluorination of the organic feed).

BRIEF DESCRIPTION OF THE DRAWINGS

The drawing is a process flow diagram of one embodiment of the inventive process.

DETAILED DESCRIPTION

Useful organic feeds include a wide variety of known substances, including those which are just slightly soluble in many inert liquid media used heretofore in liquid-phase direct fluorination, and thus require the use of Freon™ 113 chlorofluorocarbon which is a very useful inert solvent but is being phased-out and replaced by industry due to its atmospheric ozone depletion potential.

The organic feed which can be used in the practice of this invention include those, such as hydrocarbon ethers, which in some direct fluorination processes have been considered too reactive with the byproduct hydrogen fluoride produced or too fragile to withstand direct fluorination at high temperatures (such as the temperatures which can be employed in the process of the invention) in the absence of hydrogen fluoride scavenger.

The process of this invention can be carried out in a direct fluorination, tubular reactor system, described below, comprising a tubular reactor in which the fluorination of diluted organic feed is rapidly carried out and which can be used in combination with a recycle loop for recycle to the reactor of a stream of the inert liquid reaction medium under turbulent flow and mixed with the organic feed. Such a tubular reactor, providing a high ratio of reactor surface area (through which heat may be transferred) to reaction volume (in the highly exothermic and hazardous fluorination) can be efficiently temperature-controlled and has been found to be superior in that respect as compared to the stirred tank reactor used in liquid-phase direct fluorination work. The tubular reactor system of this invention also can produce liquid fluorinated products which in many cases are superior in yield, molecular weight, and (where desired) functionality.

The process of this invention can be carried out in the tubular reactor recycle loop system schematically illustrated in the drawing. For fluorinating normally liquid, organic substances, the system can comprise:

a tubular reactor, preferably of uniform cross-section, and without having any significant pressure drop along its length, in which the fluorination of the turbulent solution or dispersion of the organic feed is quickly and safely carried out;

a means to introduce fluorine gas into the tubular reactor;

a gas-liquid separator in which the reactor product stream is separated into a gaseous phase comprising unreacted fluorine, inert gas, by-product hydrogen fluoride, and any volatile fluorinated product, and a liquid phase or stream comprising the inert liquid medium and any non-volatile fluorinated product; and pumping means and associated piping or tubing to recycle liquid through the system, that is, to pass the separated inert liquid medium in turbulent flow to a tubular mixing zone (e.g., a pipe with a circular cross-section) in which the liquid medium is mixed with additional organic feed, the mixing zone being connected to the tubular reactor (which can also be a circular pipe) so as to pass or convey the resulting turbulent stream of the solution or dispersion of organic feed to the reactor into which the diluted fluorine gas is introduced under pressure.

One or preferably at least two cooling means or condensers, connected in series, can be used to condense out residual or entrained inert liquid medium and fluorinated product from the gaseous phase separated from the reactor product stream. When the organic feed fluorinated by the process of this invention is a volatile organic substance, additional equipment (such as compressors, heat exchangers, condensers, and cold traps) can be used for recovering volatile fluorinated product. Scrubbing means, such as one or preferably at least two scrubber columns connected in series, can be used to remove unreacted fluorine; gas and hydrogen fluoride from the cooled gaseous effluent and produce an inert gas effluent.

If the fluorinated product is a liquid, a take-off or slip stream can be continuously or intermittently drawn from the separated liquid phase described above, and the inert liquid medium can be distilled off or otherwise separated from the slip stream to recover fluorinated product.

The turbulent stream of the solution or dispersion of organic feed that is pumped through the mixing zone and tubular reactor will generally have a relatively high Reynolds Number, indicative of the turbulent flow conditions of the stream. Reynolds Number is a dimensionless, calculated quantity for a flowing stream and it can be expressed in the form $LV\rho/\mu$, where L is a characteristic linear dimension of the flow channel of the stream, e.g., the inside diameter of a tube, pipe, or conduit; V is the velocity or flow rate of the stream; $\rho$ is the density of the stream; and $\mu$ is the viscosity of the stream. For purposes of this description, the flow rate, density, and viscosity of the inert liquid medium (not the total mixed phased stream) flowing in the mixing zone are used to calculate the Reynolds Number. Thus, the Reynolds Number discussed in this specification and in the claims can, in a sense, be called an "apparent" Reynolds Number. The Reynolds Number of the turbulent streams of this invention will generally be at least about 3,000, preferably in the range of 6,000 to 150,000, more preferably in the range of 8,000 to 100,000.

Referring to the drawing, reference number 6 designates a jacketed, temperature-controlled gasliquid separator having an overhead conduit or pipe 7 for gas, a bottom conduit 8 for liquid, a liquid level indicator 9 for indicating the level of liquid 10, and a temperature sensor 11. Liquid level indicator 9 and temperature sensor 11, as well as the temperature and pressure sensors to be described hereinafter, can be connected to a supervisory control and data acquisition system to monitor the process and actuate appropriate control mechanisms, such as valves, pumps, electric heaters, etc., to shut down all or parts of the tubular reactor system in response to deviations from predetermined process set points.

The liquid phase separated from the reactor product passes through bottom conduit 8 to a pump 12 which is operated to discharge the liquid phase through ,discharge conduit 13, fitted with pressure sensor 14 and temperature sensor 16, to conduit 17. The latter conduit has an upstream inlet 18 and downstream inlet 19 and functions as a tubular mixing zone in which the turbulent stream is mixed with organic feed supplied via conduit 21 to inlet 18. The resulting turbulent stream of a solution or dispersion of organic feed in inert liquid medium is then contacted with a stream of fluorine gas introduced under positive pressure from its source and diluted with an inert gas such as nitrogen, the diluted stream being supplied via conduit 22 to inlet 19 at a flow rate independent of the flow rate of the turbulent liquid stream, conduit 22 being positioned, for example, so that its end is in a region of turbulence. The cross sectional area and length of the mixing zone 17 are sufficient to dissolve or disperse the organic feed in the inert liquid medium under the conditions present in the fluid stream inside the mixing zone.

The organic feed can be supplied from reservoir 23 by a pump 24 which meters and pumps the organic feed through conduit 21 which is provided with flow control valve 26 and check valve 27. Fluorine from a pressurized tank is supplied via conduit 28, fitted with pressure sensor 29, flow control valve 31, and check valve 32, and the inert gas from a pressurized tank is supplied via conduit 3.3, fitted with pressure sensor 34, flow control valve 36, and check valve 37.

Downstream of tubular mixing conduit 17 is tubular reactor 38 (which can be a plug flow reactor or pipe reactor with a circular cross-section) extending from inlet 19 where the diluted fluorine initially contacts and begins to react with the turbulent ;stream from conduit 17 to the gas-liquid separator 6 which receives the reactor product. The cross section and length of tubular reactor are such that the residence time of the stream of turbulent, gas-liquid, reaction mixture is sufficient to substantially consume the fluorine to the desired level and minimize degradation (if any) by by-product hydrogen fluoride of the organic feed (e.g., ether) or fluorinated product. Generally, the ratio of the length of the tubular reactor 38 to its inside diameter is in the range of 50:1 to 1000:1 or more. The residence time of fluid in the tubular reactor 38 is a function of volumetric flow rate through the reactor, and reactor length and diameter, each of which can be varied to achieve an optimum in the yield or selectivity of desired fluorinated product. The tubular reactor 38 provides a ratio of reactor surface for heat transfer to reaction volume, which permits control over the reaction temperature (which can be fitted with a heat-exchange jacket and a temperature sensor 39).

Reactor 38 can be horizontally or vertically disposed or inclined, and it (as well as the mixing conduit 17) can be in the form of a plurality of tubes connected at their ends to a header, as a practical matter or to increase capacity. Reactor 38, as well as mixing conduit 17, can be made from metal commonly used to conduct fluorine gas, such as Monel alloy, stainless steel, or aluminum. The reactor can be thermally insulated, wrapped with heating tape, or otherwise temperature-controlled.

The concentration of organic feed dissolved or dispersed in the stream entering the tubular reactor can be determined by one of skill in the art based on several considerations, including the characteristics of the particular feed material and inert liquid medium, heat transfer and safety factors. It is preferably dilute. One useful range (expressed as volumetric ratio of organic feed to inert liquid medium) is 1 part organic feed: 10,000 parts inert liquid medium to 1 part organic feed: 40,000 parts inert liquid.

The stream of reactor product passes from the downstream end 40 of tubular reactor 38 into gas-liquid separator 6 where the two phases (gas and liquid) separate, the gas phase being removed via overhead line 7 and the liquid phase accumulating in the lower portion of the separator and being drained via bottoms line 8. The gas phase, in the case of a liquid fluorinated product, may comprise unreacted fluorine, inert gas, by-product hydrogen fluoride, some entrained inert liquid reaction medium, possibly some volatile fluorinated product, plus possibly other non-condensible gases. The gas phase is passed via line 7 to a heat exchanger or condenser 41, using for example chilled water as a cooling medium, in which some of the residual inert reaction medium and other organic material are condensed and recycled via lines 42 and 43 to separator 6, line 43 having a liquid trap portion as shown in the drawing. A stream of gases and any non-condensed inert reaction medium and other organic material 44 flows to a second, lower temperature, heat exchanger 46 (using, for example, an ethylene glycol-water coolant) and condensed inert reaction medium and other condensed organic material are recycled via lines 45 and 43 to separator 6. Heat exchangers 41 and 46 are supplied with coolants whose temperatures are monitored by temperature sensors 47 and 48, respectively.

If the fluorinated product is normally gaseous the gaseous stream in line 49 is compressed in compressor 66 and the compressor high pressure discharge stream 65 flows into heat exchanger 67, in which the fluorinated product is condensed and separated from the non-condensible components of stream 65, and routed via line 71 and valve 72 to a collection device 76. The pressure of non-condensible stream 69 is monitored by pressure sensor 73 before it flows through pressure-reducing control valve 74. If the fluorinated product is normally liquid, the gaseous stream in line 49 bypasses compressor 66 by closing valves 81 and 74 and opening valve 82, allowing the stream to pass through line 83 to the scrubbers 52 and 53.

The non-condensible stream in line 75 is passed through a series of two scrubbers (gas adsorption or absorption apparatus) 52 and 53 containing alumina, caustic, or other suitable media to remove fluorine and hydrogen fluoride by-product from the cooled gas stream, the scrubbed gas being passed via line 54 from the last scrubber, 53. When an alumina scrubbing medium is used, oxygen measuring device 56 monitors oxygen content in the scrubbed gaseous stream in line 54. The concentration of oxygen (derived from the reaction of the alumina in the scrubbers with unreacted fluorine) in the gaseous stream in line 54 is an indication of the amount of unreacted fluorine.

When the amount of fluorinated product in the liquid stream in conduits 8 and 13 is significant or at the concentration desired, a take-off or slip stream 57 of the recycled stream can be drawn off line 13 by opening valve 58 and the slip stream is passed to a suitable recovery system, such as distillation column 59. In the distillation operation, inert reaction medium is returned as a distillate via line 61 to gas-liquid separator 6, and fluorinated product is removed as bottoms via line 62 through valve 63. The amount of the recycled liquid in line 13 that is withdrawn by slip stream line 57 can be varied, but will be relatively small, generally about 1/50 to 1/5,000 of the liquid discharged by pump 12.

Suitable liquids for use as inert liquid media are those which can function as solvents or dispersants for the organic feed and fluorinated product and which do not react appreciably with diluted fluorine. That is, the inert liquid medium should be relatively inert to fluorine at the temperatures utilized in the process.

Examples of perhallogenated organic liquids useful as the inert liquid media are: perfluoroalkantes, such as perfluorinated pentanes, hexanes, heptanes, octanes, and decalins; perfluoroethers such as those sold as Fluorinert™ FC-75 and FC-77 by Minnesota Mining and Manufacturing Company, Krytox™ by E. I DuPont de Nemours & Co., and Fomblin™; perfluorotrialkylamines such as Fluorinert™ FC-40; chlorofluorocarbons such as Freon™ 113, 1,1,2-trichlorotrifluoroethane, Freon™ 11, fluorotrichloromethane, and 1,1,3,4-tetrachlorohexafluorobutane (available as 0.8 Halocarbon Oil from Halocarbon Products Corp.); chlorofluoroethers such as perfluoro-bis(chloroethyl)ether, and perfluoropolyepichlorohydrin; perfluoroalkanesulfonyl fluorides such as perfluoro-1,4-butanedisulfonyl fluoride and perfluorobutanesulfonyl fluoride; and mixtures thereof.

These inert liquids are conveniently used at atmospheric pressure. Lower molecular weight members of the above classes can also be used, but elevated pressures may be required to provide a liquid phase. In some cases it may be feasible to use perfluorinated product as reaction medium, which may render unnecessary the separation of perfluorinated product from the inert liquid medium.

Liquids suitable for use in diluting the organic feed (prior to its addition to the turbulent stream of inert liquid reaction medium at inlet 18) include the inert liquids described above as well as liquids which may to some degree react with fluorine such as, for example, carbon tetrachloride, chloroform, and fluorinated alkanes containing one or two hydrogens, or materials which contain little or no halogen but in themselves are perfluorinateable to useful products.

Generally, reactor temperature will be maintained in the range of about 0° C. to about+150° C., preferably about 0° C. to about 85° C., most preferably about 20° C. to about 60° C., sufficient to volatilize hydrogen fluoride reaction by-product, and, with the aid of the flowing inert gas, cause the purging of the by-product HF from the gas-liquid separator 6.

The design and temperature of the separation system is such as to minimize or prevent hydrogen fluoride from returning to the reactor. This is of particular significance the case of starting materials such as ethers and olefinic materials, which may be adversely affected by hydrogen fluoride. A low yield of fluorinated organic feed can result if hydrogen fluoride is retained in the tubular reactor system during fluorination.

Fluorine in conduit 22 is preferably at a concentration of about 5 to 50 volume %, more preferably about 10 to 25 volume %, in an inert gas such as, argon, helium, $CF_4$, $SF_6$, or nitrogen. Pure fluorine can also be used but is not preferred, due to considerations of both safety and economy.

To maximize the yield of perfluorinated product, the amount of fluorine is maintained in stoichiometric excess throughout the fluorination in the reactor, for example, at an excess of up to about 15 to 50% or higher. When partially-fluorinated products are desired, lesser amounts of fluorine, can be used. In using less than a stoichiometric amount of fluorine for each pass (or "plug" of turbulent stream), some of the molecules of the organic feed may be perfluorinated, some are partially fluorinated, and some may not be fluorinated.

Although the process of this invention can be used to make perfluorinated product in which essentially all molecules of the organic feed are perfluorinated and the product may contain small amounts of fluorinated substances having one or a few residual hydrogen atoms, the product can be essentially fully fluorinated, i.e., perfluorinated, with a residual hydrogen content of less than about 0.4 mg/g and generally less than about 0.1 mg/g. The liquid phase fluorinated reaction product 8 can be distilled in distillation apparatus 59 to remove the inert liquid reaction medium and any low-boiling by-products. Fluorinated substances with residual hydrogen content and traces of undesired carboxylic acid derivatives can be removed (virtually completely) by passing fluorine, preferably diluted with inert gas through the liquid distillation bottoms at elevated temperature (eg. 150° C. or higher) to, in a sense, "polish" the product. Any resulting hydrogen fluoride and carbonyl fluorides are removed, along with the unreacted fluorine gas used. This polishing technique cannot be as effectively utilized if the desired product is a perfluorinated functional substance such as a carboxylic acid. Alternatively, non-functional perfluorinated product can be purified by washing the bottoms with a base solution, such as potassium hydroxide. Perfluorinated acid product can be purified by washing with a base, followed by acidification and distillation.

The organic substances which can be used as organic feed are those which can be fluorinated, that is, those which contain carbon-bonded hydrogen replaceable by fluorine, and they can contain carbon—carbon unsaturation which is saturatable with fluorine. Representative examples of organic substances which can be perfluorinated or partially fluorinated by the process of this invention are monoethers, such as dioctyl ether, bis(chlorobutyl) ether, bis(monofluoromethyl) ether, and dimethyl ether; polyethers, such as polyepichlorohydrin and polyethylene glycol, and other glymes, e.g., heptaethylene glycol dimethyl ether; alcohols, such as octanol and butoxyethoxyethanol; acetals, such as polydioxoane, polytrioxocane, polymethyleneoxide, polybutyrylaldehyde, bis(2-butoxyethoxy)methane, 3,6,9,11-tetraoxaheptadecane, 5,7,10,13-tetraoxaheptadecane, 2,14-dimethyl-4,7,9,12-tetraoxapentadecane, 3,6,9,11,14,17-hexaoxanonadecane, 2,5,7,10,13,16,18,21-octaoxadocosane, 3,6,8,11,14,16,19-heptaoxaheneicosane, and 3,5,8,11,14-pentaoxaoctadecane; carboxylic acid esters, such as 2-methylbutyl acetate, dimethyl adipate, caprolactone, methyl caprylate, n-octyl acetate, n-octadecyl acetate, methyl benzoate, polyethylene glycol bis(trifluoroacetate), tetraethylene glycol diacetate, 2-(2-ethoxy)ethoxyethyl acetate, polyethylene glycol monomethylether monoacetate, polyethylene glycol diacetate, 2-(2-butoxyethoxy)ethyl acetate, 2-methoxyethylacetate, and polytetramethylene glycol diacetate; sulfonyl fluorides, such as octanesulfonyl fluoride; acid fluorides, such as octanoyl fluoride and benzoyl fluoride; and sulfonate esters such as methyl octanesulfonate; chlorohydrocarbons, such as 1,8-dichlorooctane; hydrocarbons, such as ethane; and fluorohydrocarbons, such as tetrafluorotetrahydrocyclobutane. U.S. Pat. No. 5,093,432 contains a description of a wide variety and many different classes of hydrogen-containing materials which can be fluorinated by the liquid-phase process described therein, including ethers, acyl halides, alkanes, etc., and said description is incorporated herein by reference as organic feeds useful in the practice of this invention.

As indicated earlier, a host of the fluorinated organic substances that can be prepared by the practice of this invention and their utilities are known. For example, the perfluorinated ethers can be prepared by the process of this invention as inert fluids useful as hydraulic fluids, heat transfer fluids, pump fluids for corrosive environments, and fluids for vapor phase condensation heating for soldering and for polymer curing applications. The perfluorinated carboxylic acid derivatives and sulfonic acid derivatives are useful, for example, as precursors to fluoroalcohol acrylates, for chemical or physical incorporation into or treatment of hydrocarbon materials to impart fluorochemical properties thereto, and they may be converted to acids which are, as well as their salts, useful as surface active agents. The perfluorinated ether acids are useful for polymer curing applications and for conversion to inert perfluorinated ether fluids.

This invention is further illustrated by the following examples, but the particular materials and amounts thereof recited in these examples, as well as other conditions and details, should not be construed to unduly limit this invention. In the runs described in the examples, no attempt was made to optimize, the yield or functionality of the fluorinated substances.

In the examples, various organic substances were prepared according to this invention, using a tubular reactor system like that described above and illustrated in the drawing. In that system, a 2 liter gas-liquid separator 6 was used to separate the fluorination reaction product from the tubular reactor 38. Liquid 8 drained from the separator was passed to a variable speed (0 to 3 gal/min or 0 to 11.4 l/min) gear pump 12. The liquid discharged from pump 12 flowed through tubing 13 (made of Monel alloy), past a pressure transducer 14 and temperature sensor 16, and then entered the mixing zone 17 of the tubing. In the mixing zone 17 a Reynolds Number in excess of 4000 could be obtained, and the diameter of the tubing of this zone was varied between ¼ to ¾ inch (6 mm to 19 mm) and the length varied between 6 inches and 20 feet (15 cm to 6 meters). Diluted fluorine 22 was introduced into reactor 38. The diameter of the tubular reactor was varied between ¼ to ¾ inch (6 to 19 mm) and the length of the reactor was varied between 2 and 20 feet (60 cm to 6 m). In all of the examples of this invention, except as indicated, the liquid fluorinated product recovery system was used (namely, the tubular reactor system shown in the drawing in which the gaseous effluent from heat exchanger 46 is passed via lines 49, 83, and 75 to scrubber column 52, by-passing compressor 66 and heat exchanger 67 of the gaseous product recovery system).

EXAMPLE 1

Perfluorination of Poly(tetramethylene oxide) Diacetate

A perfluorination tun was started by initially charging the gas-liquid separator 6 of the reactor system with 2 L of Fluorinert™ FC-77 inert liquid medium and circulating it through the reaction system at 3 gal/min (11.4 L/min). Nitrogen was introduced into the circulating stream of inert liquid at a rate of 1200 sccm and the temperature of the circulating liquid maintained at 50° C. The two overhead condensers 41 and 46 were maintained at 0° C. and −25° C., respectively. Fluorine was introduced into the tubular reactor at 300 sccm after the nitrogen purged the system to an oxygen concentration in the scrubber effluent of<0.10%, as measured by the oxygen sensor (56). A feed of 121 g of poly(tetramethylene oxide) diacetate (334 molecular weight (MW)) was introduced into the mixing zone during a period of 20 hours. Upon complete addition of the diacetate feed, the diluted fluorine addition was continued until the oxygen concentration of the scrubber effluent rose to>5.0%. The fluorine supply was shut off and nitrogen supply continued until the oxygen concentration had dropped to<0.10%, after which the circulation pump 12 was turned off. The liquid phase contents of the gas-liquid separator were drained (via line 15), mixed with 95 g of methanol, washed with water, and the lower phase dried over MgSO$_4$. Distillation of the FC-77 inert liquid from the liquid phase produced 149 g (59% yield) of liquid perfluoropoly(tetramethylene oxide) dimethyl ester product. Gas chromatographic analysis confirmed the product to be essentially a mixture of compounds of the formula CH$_3$OCOC$_3$F$_6$O(C$_4$F$_8$O)$_n$C$_3$F$_6$COOCH$_3$ in which n ranged from 0 to 5. The average molecular weight of the product was 554 and the average functionality was 1.7 (determined by $^{19}$F NMR (nuclear magnetic resonance)).

COMPARATIVE EXAMPLE A

Perfluorination of Poly(tetramethylene oxide) Diacetate Using a Stirred Tank Reactor A comparative direct fluorination was done using the 2 L. stirred tank reactor described in PCT publication WO 90/06296 (Costello et al.). The reactor was charged with about 1.8 L. of Fluorinert™ FC-77 inert fluid and maintained at 50° C. After purging the reactor with nitrogen, fluorine was introduced at a rate of 280 sccm and nitrogen at a rate of 1200 sccm. A feed of 125 g of poly(tetramethylene oxide) diacetate (334 MW) was introduced into the reactor over a period of 21 hours. At the end of the fluorination, 94 g of methanol was added to the reactor and the contents stirred for one hour. The contents of the reactor were drained, washed with water, the lower phase dried over MgSO$_4$, and the inert fluid distilled off to produce 63 g (24% yield) of perfluoropoly(tetramethylene oxide) dimethyl ester product, which was found to have an average molecular weight of 503 and a functionality of 1.9.

By comparison, the, 59% yield obtained in the inventive process of Example 1 was substantially better than the 24% yield of Comparative Example A.

EXAMPLE 2

Perfluorination of Poly(ethylene oxide) Diacetate Using Tubular Reactor System Gas liquid separator 6 was charged with 2 L. of 1,1,3,4-tetrachlorohexafluorobutane and the reactor system purged with nitrogen, as in Example 1. The inert liquid medium was circulated at 2 gal/min (7.6 l/min). Fluorine and nitrogen were introduced as in Example 1. An organic feed of 120 g of poly(ethylene oxide) diacetate (MW 684) was added during 20 hours as the temperature of the circulating fluid was maintained at 60° C. The product was isolated as in Example 1, and it amounted to 187 g (70% yield) of essentially CH$_3$OCOCF$_2$O(C$_2$F$_4$O)$_n$CF$_2$COOCH$_3$, in which n was 6 to 14, having an average molecular weight of 1110 and a functionality of 1.1.

COMPARATIVE EXAMPLE B

Perfluorination of Poly(ethylene oxide) Diacetate Using a Stirred Tank Reactor A comparative direct fluorination of 150 g of poly(ethylene oxide) diacetate (MW 684) was run for 20 hours in a stirred tank reactor as in Comparative Example A, using 1,1,3,4-tetrachlorohexafluorobutane as the inert fluid and a reactor temperature of 50° C. The product, CH$_3$OCOCF$_2$O(C$_2$F$_4$O)$_n$CF$_2$COOCH$_3$ (in which n was 6 to 14) was obtained and isolated as in Comparative Example A and it amounted to 119 g (35% yield) with an average molecular weight of 1166 and a functionality of 1.5.

The 70% yield of the inventive process in Example 2 was substantially better than the 35% yield of Comparative Example B.

EXAMPLES 3–13

Perfluorination of Other Acetates Using Tubular Reactor System

A number of other acetates were directly fluorinated in the tubular reactor system of this invention, as in Examples 1 and 2, and those fluorinations are summarized in Table 1 along with Examples 1 and 2.

In a similar comparative run in the stirred tank reactor, maintained at 45° C., the isolated Cl—$C_8F_{16}$—Cl product amounted to 116 g (45% yield).

As can be seen by comparing the results of the runs of Comparative Example C and Example 14, yields of an inert fluorinated product may be obtained using the process of this invention that are higher than that obtained using a stirred tank reactor.

TABLE 1

| | Materials | | | | | Reaction Conditions | | | | Functional Perfluorinated Product | | |
|---|---|---|---|---|---|---|---|---|---|---|---|---|
| | Organic | Feed Rate | Inert | $F_2$ | $N_2$ | Circulation | Reynolds | Temp. | Run | | | |
| Ex. | Feed Type* | Average (ml/hr) | Liquid Type** | Rate (sccm) | Rate (sccm) | Rate (L/min) | No. (calc.) | Ave. (°C.) | Time (hrs) | MW*** | Func- tionality | Yield (%) |
| 1 | PTMO-334 | 6 | FC-77 | 300 | 1200 | 11.8 | 22562 | 52 | 20 | 554 | 1.7 | 59 |
| 2 | PEG-684 | 6 | CTFE | 270 | 1200 | 7.6 | 19192 | 61 | 20 | 1110 | 1.1 | 70 |
| 3 | PEG-384 | 6 | FC-77 | 250 | 1000 | 9.5 | 18195 | 60 | 23 | 560 | 1.5 | 51 |
| 4 | PEG-684 | 6 | R-113 | 310 | 1200 | 11.8 | 41715 | 18 | 19.2 | 762 | 1.3 | 62 |
| 5 | PEG-684 | 6 | PNMM | 250 | 1000 | 12.9 | 24745 | 25 | 22 | 565 | 0.8 | 29 |
| 6 | PEG-684 | 22 | CTFE | 800 | 4000 | 5.7 | 7840 | 60 | 15 | 1117 | 1.1 | 47 |
| 7 | PTMO-334 | 6 | FC-77 | 300 | 1200 | 11.8 | 22562 | 33 | 20.7 | 531 | 1.9 | 57 |
| 8 | PTMO-334 | 6 | FC-77 | 300 | 1200 | 11.4 | 21980 | 55 | 20.5 | 590 | 1.2 | 67 |
| 9 | PTMO-334 | 6 | R-113 | 300 | 1200 | 3.8 | 13457 | 18 | 20 | 645 | 1.9 | 88 |
| 10 | PTMO-734 | 6 | CTFE | 300 | 1200 | 7.6 | 19192 | 61 | 22.8 | 1430 | 1.6 | 83 |
| 11 | MEA | 24 | FC-75 | 900 | 3000 | 7.6 | 7928 | 32 | 20.2 | 194 | 1.0 | 42 |
| 12 | BEEA | 5 | FC-77 | 250 | 1300 | 9.5 | 10022 | 39 | 69 | 460 | 1.0 | 59 |
| 13 | OA | 21 | FC-77 | 850 | 3500 | 9.5 | 10022 | 35 | 5 | 428 | 1.0 | 36 |

*Description of type of organic feed:
"PTMO" means poly(tetramethylene oxide) diacetate and the number following it is its mol. wt..
"PEG" means poly(ethylene oxide) diacetate and the number following it is its mol. wt.
"MEA" means methyoxyethylacetate
"BEEA" means 2-(butoxyethoxy)ethylacetate
"OA" means octylacetate
**Description of type of inert liquid used as reaction medium:
"FC-77" means Fluorinert ™ 77
"CTFE" means 1,1,3,4-tetrachlorohexafluorobutane
"R-113" means Freon ™ 113
"PNMM" means perfluoro-N-methylmorpholine
"FC-75" means Fluorinert ™ 75
***Mol. Wt. ("MW") given is that of fluorinated product as the methyl ester

EXAMPLE 14

Perfluorination of 1,8-dichlorooctane Using Tubular Reactor System

The gas-liquid separator 6 was charged with 2 L of Fluofinert™ FC-77 inert liquid medium, which was circulated at a rate of 2 gal/min (7.6 L/min) and maintained at 45° C. Organic feed of 694 g of 1,8-dichlorooctane was introduced into the mixing zone 17 over a period of 116 hours, and nitrogen and fluorine were supplied at flow rates given in Example 1. Upon complete addition of the feed, the contents of the gas-liquid separator were drained and the inert fluid distilled therefrom to produce 1537 g (86% yield) of a product which was essentially Cl—$C_8F_{16}$—Cl.

COMPARATIVE EXAMPLE C

Perfluorination of 1,8-dichlorooctane Using a Stirred Tank Reactor

A comparative direct fluorination of 100 g of 1,8-dichlorooctane was carried out as in Comparative Example A, except that the feed was added to the stirred tank reactor over a period of 20 hours and the fluid temperature was maintained at 65° C. The reactor contents were drained and 209 g (81% yield) of the product, essentially Cl—$C_8F_{16}$—Cl, was isolated by distillation.

COMPARATIVE EXAMPLE D

Perfluorination of 1,8-dichlorooctane Under Non-turbulent Conditions Using a Tubular Reactor System The significance of the turbulent flow requirement of this invention was shown in this comparative example by running the fluorination reaction of Example 14 under non-turbulent flow conditions (that is, a relatively low Reynolds Number). The gas-liquid separator was charged with Fluofinert™ FC-77 inert liquid medium as in Example 14 and the medium circulated at a rate of 0.5 gal/min (1.9 L/min) at 60° C., the Reynolds Number of the circulating fluid being 2551. A feed of 136 g of 1,8-dichlorooctane was introduced into the reactor over 22 hours at the same flow rates of fluorine and nitrogen and oxygen as in Example 14. Upon complete addition of the feed, the contents of the gas-liquid separator was drained; 40 g (12% yield) of the Cl—$C_8F_{16}$—Cl product was isolated by distillation.

As can be seen by comparison of Comparative Example D with Example 14, fluorination of a feed under non-turbulent flow conditions leads to poor yields of the desired fluorinated material.

EXAMPLES 15–26

Other Perfluorinations of Inert Substances Using Tubular Reactor System

In these examples, 1,8-dichlorooctane and bis(butoxyethoxy)methane were perfluorinated according to this invention and these perfluorinations are summarized in Table 2 along with that of Example 14.

some unreacted ethane, as determined by gas chromatography. No attempt was made to isolate species of interest, e.g., $C_2HF_5$, from the mixture.

TABLE 2

| | Materials | | | | | Reaction conditions | | | | Inert |
|---|---|---|---|---|---|---|---|---|---|---|
| Ex. | Organic Feed Type* | Feed Rate Average (ml/hr) | Inert Liquid Type** | $F_2$ Rate, (sccm) | $N_2$ Rate (sccm) | Circulation Rate (L/min) | Reynolds No. (calc.) | Temp., Ave. (°C.) | Run Time, (hrs) | Perfluorinated Product, Yield (%) |
| 14 | 1,8-DCO | 6 | FC-77 | 300 | 1200 | 7.6 | 14556 | 45 | 116 | 86 |
| 15 | 1,8-DCO | 6 | FC-77 | 300 | 1200 | 11.4 | 15309 | 61 | 23 | 79 |
| 16 | 1,8-DCO | 6 | FC-77 | 300 | 1200 | 11.4 | 15309 | 11 | 22 | 69 |
| 17 | 1,8-DCO | 14 | FC-77 | 650 | 2400 | 11.4 | 15309 | 50 | 21 | 73 |
| 18 | 1,8-DCO | 12 | FC-77 | 600 | 2400 | 11.4 | 15309 | 72 | 14 | 75 |
| 19 | 1,8-DCO | 20 | FC-77 | 1000 | 4000 | 11.4 | 15309 | 86 | 23 | 72 |
| 20 | 1,8-DCO | 50 | FC-77 | 1600 | 7200 | 11.4 | 11892 | 65 | 8 | 70 |
| 21 | BEM | 6 | R-113 | 300 | 1200 | 11.4 | 40370 | 20 | 20 | 62 |
| 22 | BEM | 6 | FC-77 | 280 | 1200 | 9.5 | 18195 | 63 | 17 | 70 |
| 23 | BEM | 9 | FC-77 | 420 | 1800 | 9.5 | 18195 | 63 | 22 | 64 |
| 24 | BEM | 6 | FC-77 | 300 | 1200 | 11.4 | 21834 | 49 | 23 | 61 |
| 25 | BEM | 6 | FC-77 | 300 | 1200 | 3.8 | 10776 | 49 | 22 | 65 |
| 26 | BEM | 6 | FC-77 | 300 | 1200 | 7.6 | 10206 | 50 | 48 | 58 |

*Description of type of organic feed:
"1,8-DCO" means 1,8-dichlorooctane, and
"BEM" means bis(2-butoxyethoxy)methane

EXAMPLE 27

Partial Fluorination of Ethane

Illustrating the applicability of the tubular reactor system of this invention in making partially-fluorinated substances, the gas-liquid separator was charged with 2 L of Fluorinert™ FC-75 inert liquid medium which was then circulated at a rate of 1.5 gal/min (5.7 L/min) and maintained at 20° C. Organic feed of 1445 g of ethane was added to the mixing zone 17 over a period of 16 hours and reacted with the fluorine supplied at a flow rate of 200 sccm and nitrogen being supplied at a flow rate of 3000 sccm. The reactor product stream was separated using the gaseous product recovery system (including the compressor 66 and heat exchanger 67) to produce a mixture of hydrofluoroethanes of the structure $C_2H_nF_{6-n}$ (wherein n ranged from 0 to 5) and

EXAMPLES 28–32

Partial Fluorination of Other Inert Substances Using Tubular Reactor System

Additional examples describing the partial fluorination of other substances according to this invention are summarized in Table 3 along with Example 27.

TABLE 3

| | Materials | | | | | Reaction conditions | | | |
|---|---|---|---|---|---|---|---|---|---|
| Ex. | Organic Feed Type | Feed Rate Ave. (ml/hr) | Inert Liquid Type*** | $F_2$ Rate (sccm) | $N_2$ Rate (sccm) | Circulation rate (L/min) | Reynolds No. (calc.) | Reactor Temp. Ave. (°C.) | Run Time (hrs) |
| 27 | ethane | 35 | FC-75 | 200 | 3000 | 5.7 | 5946 | 20 | (days) |
| 28 | R-134a* | NA | FC-77 | 60 | 600 | 8.4 | 15940 | 50 | (weeks) |
| 29 | $cC_4F_4H_4$* | 4.0 | FC-77 | 300 | 1200 | 5.7 | 11420 | 57 | 12.0 |
| 30 | BFME* | 15.9 | FC-75 | 340 | 3000 | 9.5 | 9910 | 25 | 4.2 |
| 31 | $CH_3OCH_3$ | 18 | FC-75 | 200 | 3000 | 3.8 | 3964 | 20 | 3.5 |
| 32 | $CH_3OCH_3$ | 18.7 | FC-75 | 300 | 2000 | 3.8 | 3964 | 26 | 6.9 |

*Description of type of organic feed:
"R-134a" means 1,1,1,2-tetrafluoroethane
"BFME" means bis(monofluoromethyl)ether
"$cC_4F_4H_4$" means tetrafluorocyclobutane

EXAMPLE 33

Perfluorination of N-octylsulfonyl Fluoride Using Tubular Reactor System

The gas-liquid separator was charged with 2 L of Fluofinert™ FC-77 inert liquid, circulated at a rate of 2.5 gal/min (9.5 L/min), with a corresponding Reynolds No. of 18,800 and maintained at 30° C. Organic feed of 118 g of n-octylsulfonyl fluoride was added to the mixing zone over a period of 22 hours, and nitrogen and fluorine were supplied at flow rates of 2000 and 200 sccm, respectively. Upon complete addition of the feed, the contents of the gas-liquid separator were drained and the inert fluid was stripped therefrom, resulting in 46 g of a concentrated perfluoro-n-octylsulfonyl fluoride product having a purity of 48% as determined by gas chromatography.

EXAMPLE 34

Perfluorination of 1,8-dichlorooctane Using Tubular Reactor System Including Continuous Take-off, Distillation, and Solvent Recycle The gas-liquid separator 6 of the reactor system was charged with 2 L of Fluofinert™ FC-77 inert fluid which was circulated through the system at a rate of 2.5 gal/min (9.5 L/min). Nitrogen was added to the circulating stream of inert liquid medium at a rate of 800 sccm and the temperature of the circulating fluid was maintained at 58° C. The two overhead condensers 41 and 46 were maintained at 0° C. and −25° C., respectively. Fluorine was introduced into the tubular reactor 38 at 150 sccm after the nitrogen purged the, system to an oxygen concentration in the scrubber discharge 54 of less than 0.10% as measured by the oxygen sensor 56.

A feed rate of 4 ml/hr of 1,8-dichlorooctane was maintained during the experiment. Fluorinated product was accumulated in the circulating solvent until a concentration of about 13% by weight was achieved. Take-off was initiated by opening valve 58 and transferring material via a slip stream 57 to a 1 inch (2.54 cm) diameter glass distillation column 59, wherein Fluorinert™ FC-77 inert fluid was refluxing at a temperature of 100° C. A reflux ratio (ratio of reflux in distillation column 59 to distillate 61) of 5 to 1 was set on the timer which determined the flow rates through conduit 57 (take-off) and conduit 61 (solvent recycle). Heat (375 watts) was supplied to the reboiler of column 59 during the continuous distillation, take-off, and solvent recycle operation. Over the duration of the run, a temperature rise in the reboiler of column 59 was observed, which indicated an accumulation of the higher boiling point product. Final purification of the crude material resulted in a yield of 74% perfluoro-1,8-dichlorooctane in stream 62.

What is claimed is:

1. A tubular reactor system comprising:

A. a tubular reactor;

B. means to introduce fluorine gas into the tubular reactor;

C. a gas-liquid phase separator connected to the tubular reactor to receive the reactor product stream therefrom and separate gaseous and liquid phases of such stream;

D. a first conduit attached to the gas-liquid separator by which the liquid phase may exit the separator:

E. a pumping means, operating under turbulent flow conditions, to convey the liquid phase by means of the first conduit from said separator to be recycled to the tubular reactor by means of a second conduit connected to the discharge of the pumping means such that turbulent flow conditions, characterized by a Reynolds number of at least about 3,000, are present in the tubular reactor; and F. means to introduce organic feed which can be fluorinated into the recycle stream.

2. The tubular reactor system of claim 1 in which the ratio of the length of the tubular reactor to its inside diameter is in the range of about 50:1 to 1000:1.

* * * * *